United States Patent [19]

Adams et al.

[11] Patent Number: 5,529,897
[45] Date of Patent: Jun. 25, 1996

[54] NON-IONIC SURFACE ACTIVE COMPOUNDS

[75] Inventors: Katie E. Adams, Watford; Ian M. Newington, High Wycombe; Alan R. Pitt, St. Albans, all of United Kingdom

[73] Assignee: Eastman Kodak Company, Rochester, N.Y.

[21] Appl. No.: 485,892

[22] Filed: Jun. 7, 1995

[30] Foreign Application Priority Data

Jun. 17, 1994 [GB] United Kingdom .................. 9412140

[51] Int. Cl.$^6$ ..................................................... G03C 1/38
[52] U.S. Cl. .......................... 430/628; 430/546; 430/631; 430/637; 430/638
[58] Field of Search ............................... 430/546, 607, 430/613, 637, 638, 631, 628

[56] References Cited

U.S. PATENT DOCUMENTS

| | | | |
|---|---|---|---|
| 3,396,028 | 8/1968 | Humphlett | 430/613 |
| 5,037,973 | 8/1991 | Meinetsberger | 536/53 |
| 5,270,161 | 12/1993 | Pitt et al. | 430/637 |
| 5,300,418 | 4/1994 | Visconte et al. | 430/631 |
| 5,370,986 | 12/1994 | Lok et al. | 430/614 |
| 5,403,922 | 4/1995 | Garelli-Calvet et al. | 536/1.11 |
| 5,457,023 | 10/1995 | Briggs et al. | 430/631 |

FOREIGN PATENT DOCUMENTS

| | | |
|---|---|---|
| 312087 | 4/1989 | European Pat. Off. . |
| 470101 | 2/1992 | European Pat. Off. . |
| 541467 | 5/1993 | European Pat. Off. . |
| 603944 | 6/1994 | European Pat. Off. . |
| 0041037 | 3/1985 | Japan ..................................... 430/607 |
| 5/117216 | 5/1993 | Japan . |
| WO90/12782 | 11/1990 | WIPO . |

OTHER PUBLICATIONS

Analytical Biochemistry, vol. 130, No. 2, 1983, New York US, pp. 485–490, Leonard M. Hjelmeland et al., "A New Class of Nonionic Detergents With A Gluconamide Polar Group".
Chemical Abstract No. CA118(14):126983w.
Chemical Abstract No. CA82(11):73363y.

*Primary Examiner*—Lee C. Wright
*Attorney, Agent, or Firm*—Andrew J. Anderson

[57] ABSTRACT

A water-soluble or water-dispersible, non-ionic surface active compound has the formula $$ZNHQNHZ \qquad (I)$$

wherein each Z independently is a polysaccharide group linked to the remainder of the molecule through one of its ketone groups; and, Q together with the two NH groups to which it is attached represents the atoms necessary to complete a polyalkyleneamine unit wherein at least one of the amine nitrogen atoms has a hydrophobic, substituted or unsubstituted hydrocarbon group linked thereto. Such surfactants can be used in hydrophilic colloid compositions in the manufacture of photographic materials.

7 Claims, No Drawings

NON-IONIC SURFACE ACTIVE COMPOUNDS

FIELD OF THE INVENTION

The invention relates to non-ionic surface active compounds.

BACKGROUND OF THE INVENTION

Many non-ionic surface active compounds are known including compounds comprising hydrophilic groups derived from sugars. For example, EP-A-0 541 467 describes surface active compounds comprising a hydrophobic polyalkyleneamine chain having a saccharide group at each end. It is speculated that such compounds may be of use in cosmetics and pharmacy. The ability of the compounds to form vesicular structures suggests their use as encapsulating agents and also their use in the extraction of membrane proteins and in immunology.

A small proportion of known surface active agents are suitable as coating aids or dispersing aids in the preparation of photographic materials. For example, EP-A-0 314 425 describes surface active agents comprising two hydrophilic polyhydroxyalkyl chains and two hydrophobic hydrocarbon chains.

PROBLEM TO BE SOLVED BY THE INVENTION

There is a need for alternative non-ionic surface active compounds which can be used as agents to lower surface tension, wetting aids, emulsifiers, dispersing aids, coating aids and modifiers of rheology of disperse systems stabilized by ionic surfactants or polymeric surfactants.

There is a need to provide non-ionic surface active compounds which provide lower surface tension values than the compounds of EP-A-0 541 467.

Problems associated with the known compounds of EP-A-0 314 425 which are suitable for use in the manufacture of photographic materials include a lack of ease of synthesis and a lack of biodegradability.

SUMMARY OF THE INVENTION

The invention provides a water-soluble or water-dispersible, non-ionic surface active compound having the formula $$ZNHQNHZ \quad (I)$$

wherein
each Z independently is a polysaccharide group linked to the remainder of the molecule through one of its carbonyl groups; and,
Q together with the two NH groups to which it is attached represents the atoms necessary to complete a polyalkyleneamine unit wherein at least one of the amine nitrogen atoms has a hydrophobic hydrocarbon group linked thereto.

In another aspect, the invention provides a coating composition comprising a hydrophilic colloid and a surface active compound according to formula (1) above.

The invention also provides a photographic material comprising a support having thereon at least one layer comprising a hydrophilic colloid and a surface active compound according to formula (1) above.

ADVANTAGEOUS EFFECT OF THE INVENTION

Surface active compounds in accordance with the invention provide lower surface tension values than the compounds of EP-A-0 541 467.

Surface active compounds in accordance with the invention are more easily synthesized and are more biodegradable than the prior art compounds of EP-A-0 314 425.

DETAILED DESCRIPTION OF THE INVENTION

The surface active compounds of the invention may be regarded as non-ionic surfactants comprising two hydrophilic groups, each derived from a polysaccharide sugar, separately linked to one or more hydrophobic groups by a polyalkyleneamine unit.

Preferred compounds of the invention have the formula

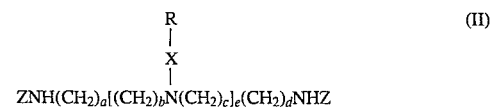

wherein
Z is as defined above;
R is a hydrophobic hydrocarbon group;
X is a linking group;
a, b, c and d each independently represents an integer from 1 to 5; and,
e represents an integer from 1 to 8.

The polysaccharide group represented by Z may be selected from di-, tri-, tetra- and oligosaccharides. For example, Z can be a disaccharide group represented by the structure

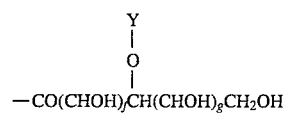

wherein
Y is a monosaccharide; and,
f and g each independently represents 0 or an integer from 1 to 3 provided that the sum of f and g is 3. Examples of Y include glucose, galactose and mannose e.g.

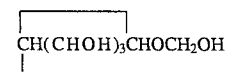

Each hydrophobic group represented by R preferably contains from 10 to 20 carbon atoms. The total number of carbon atoms in the R groups is preferably from 10 to 40. Preferred R groups include alkyl, alkenyl, allyl and aryl groups. The hydrophobic hydrocarbon groups may be substituted or unsubstituted. Suitable substituents include halo groups e.g. fluoro groups, alkyl groups e.g. $C_1$–$C_4$ alkyl and aryl groups e.g. phenyl. Specific examples of R groups are dodecyl, tridecyl and octadecyl.

Preferred linking groups represented by X are

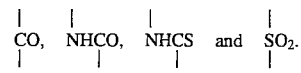

Preferred compounds include those wherein e is an integer from 1 to 4.

The compounds of the invention can be prepared by reacting together in the appropriate molar ratios (a) a polyalkyleneamine, (b) a polysaccharide C1 ester and (c) a derivative of a hydrophobic hydrocarbon compound which will react, directly or indirectly through known linking chemistry, with the NH group or groups of the polyalkyleneamine to form a linking group through which the polyalkyleneamine is linked to a hydrophobic hydrocarbon group.

An example of a suitable polyalkyleneamine has the formula $H_2N(CH_2)_a-\{(CH_2)_bNH(CH_2)_c\}_e-(CH_2)_dNH_2$ wherein a, b, c, d and e are as hereinbefore defined.

Suitable derivatives of a hydrophobic hydrocarbon compound include isocyanates (e.g. R—NCO), isothiocyanates (e.g. R—NCS), sulphonyl halides (e.g. R—SO$_2$X' wherein X' is F, Cl or Br) and carboxylic acid derivatives such as mixed anhydrides and reactive esters (e.g. R—COOX" wherein X" represents an activating group such as COOCH$_2$CH$_3$ or succinimido).

An example of a suitable polysaccharide C1 ester is the following disaccharide C1 ester

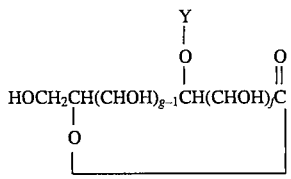

wherein Y, f and g are as hereinbefore defined.

The reactions can be carried out in solution using an organic solvent such as dimethylformamide (DMF) at a temperature from 20° to 80° C.

(a) and (b) can be reacted together and the intermediate product isolated before subsequent reaction with (c).

Alternatively, (a) and (b) can be reacted together and subsequently (c) can be added without isolation of the intermediate product.

The compounds of the invention may be used as emulsifying agents. For example, oil-in-water emulsions can be prepared by mixing the oil and water together in the presence of a compound of the invention.

The compounds of the invention may be used as coating aids in aqueous hydrophilic colloid compositions e.g. a gelatin solution. In a particular application, the compounds may be used in the preparation of light sensitive photographic materials. Such a material comprises a support having thereon at least one layer comprising a hydrophilic colloid and a compound of the invention.

In the preparation of a photographic material, it is usual to coat a support with one or more layers comprising an aqueous solution of a hydrophilic colloid binder e.g. gelatin. Such layers include, for example, silver halide emulsion layers, intermediate layers, antihalation layers, filter layers, antistatic layers and protective layers. For multilayer materials, the layers may be coated simultaneously on conventional photographic supports as described in U.S. Pat. Nos. 2,761,791 and 3,508,947.

In producing the thin hydrophilic colloid layers of such photographic materials, it is required that coating solutions are coated uniformly without the formation of repellency spots or craters, hereinafter referred to as repellencies. A repellency is a round, oval-shaped or comet-shaped indentation or crater in the layer or one or more of the layers coated and is usually produced by the presence of small particles or droplets of insoluble materials in the form of addenda, impurities or contaminants which are in contact with the uppermost liquid-air interface of the coated layer(s) and have surface activity (i.e. are capable of reducing the surface tension of the liquid-air interface during the coating process).

Solutions coated in the preparation of photographic materials often contain dispersed, insoluble photographic addenda, which might include organic solvents, or addenda to alter certain physical properties, which might include lubricants, each of which may be capable of imparting repellencies to the coated layer(s). Even photographic gelatin may contain insoluble residues of naturally-occurring animal fats and fatty acids which are capable of imparting repellencies to the coated layer(s). Also, surface active contaminants may originate from external sources during the preparation of the coating composition or during coating. For example, the layer(s) being coated, or immediately after coating, may be unintentionally showered by droplets of lubricating oils used in the apparatus.

In one aspect of the invention, a surface active compound of the invention is used as a coating aid in the formation of a hydrophilic colloid layer. Preferably, the coating aid is used in an amount from 0.01 to 0.30, more preferably from 0.05 to 0.20, weight % based on the weight of the hydrophilic colloid coating composition. The range of concentration within which the coating aid is used depends on the source of repellency. It also depends on whether other surface active agents are present.

Being non-ionic, the surface active compounds of the invention do not cause increases in viscosity when added to charged polyelectrolyte systems. In fact, they actually lower viscosity when added to aqueous complexes of ionic surfactant and gelatin. If an oil dispersion is also present in the complex mixture, the lowering of viscosity is particularly effective at low shear. Thus, the surface active compounds of the invention may be used advantageously in combination with an ionic surfactant e.g. an anionic surfactant.

The preferred hydrophilic colloid is gelatin e.g. alkali-treated gelatin (cattle bone or hide gelatin) and acid-treated gelatin (pigskin gelatin) or a gelatin derivative e.g. acetylated gelatin and phthalated gelatin. Other suitable hydrophilic colloids include naturally occurring substances such as proteins, protein derivatives, cellulose derivatives e.g. cellulose esters, polysaccharides e.g. dextran, gum arabic, zein, casein and pectin, collagen derivatives, agar-agar, arrowroot and albumin. Examples of suitable synthetic hydrophilic colloids include polyvinyl alcohol, acrylamide polymers, maleic acid copolymers, acrylic acid copolymers, methacrylic acid copolymers and polyalkylene oxides.

In the following discussion concerning the nature of photographic materials, reference will be made to Research Disclosure, December 1978, Item 17643, published by Industrial Opportunities Ltd., The Old Harbourmaster's, 8 North Street, Emsworth, Hants P010 7DD, U.K. This publication will be identified hereafter as "Research Disclosure".

The photographic material may comprise a negative-working or positive-working silver halide emulsion layer. Suitable emulsions and their preparation are described in Research Disclosure Sections I and II and the publications cited therein. Suitable vehicles for the emulsion layers and other layers of elements of this invention are described in Research Disclosure Section IX and the publications cited therein.

For color photographic materials, references giving information on couplers and on methods for their dispersions are given in Sections VII and XIV, respectively, of Research Disclosure. An account of dye-forming development is given in 'Modern Photographic Processing', Vol. 2, Grant Haist, Wiley, New York, 1978, Chapter 9.

The photographic materials or individual layers thereof, can contain brighteners (see Research Disclosure Section V), antifoggants and stabilizers (see Research Disclosure Section VI), antistain agents and image dye stabilizer (see Research Disclosure Section VII, paragraphs I and J), light absorbing and scattering materials (see Research Disclosure Section VIII), hardeners (see Research Disclosure Section XI), plasticizers and lubricants (see Research Disclosure Section XII), antistatic agents (see Research Disclosure Section XIII), matting agents (see Research Disclosure Section XVI) and development modifiers (see Research Disclosure Section XXI).

The photographic materials can be coated on a variety of supports as described in Research Disclosure Section XVII and the references described therein.

The photographic materials can be exposed to actinic radiation, typically in the visible region of the spectrum, to form a latent image as described in Research Disclosure Section XVIII and then processed to form a visible dye image as described in Research Disclosure Section XIX. Processing to form a visible dye image includes the step of contacting the element with a color developing agent to reduce developable silver halide and oxidize the color developing agent. Oxidized color developing agent in turn reacts with the coupler to yield a dye.

With negative working silver halide emulsions this processing step leads to a negative image. To obtain a positive (or reversal) image, this step can be preceded by development with a non-chromogenic developing agent to develop exposed silver halide, but not form dye, and then uniform fogging of the element to render unexposed silver halide developable. Alternatively, a direct positive emulsion can be employed to obtain a positive image.

Development is followed by the conventional steps of bleaching, fixing, or bleach-fixing, to remove silver and silver halide, washing and drying.

Specific examples of the preparation of compounds of the invention are as follows.

EXAMPLE 1

Synthesis of N4-Octadecanoyl-N1,N7-Diethylenetriaminebislactobionamide (1)

Diethylenetriamine (1.03 g, 10 mmol) and lactobionic acid (7.52 g, 21 mmol) were dissolved in methanol (750 ml) and heated under reflux for 24 hours. The solution was cooled and the solvent evaporated under reduced pressure and product freeze dried to give N1,N7-diethylenetriaminebislactobionamide as a crystalline yellow solid in 83% yield. Spectroscopic data was consistent with product.

Octadecanoic acid (stearic acid, 2.84 g, 12 mmol) was dissolved in diethyl ether (10 ml) and cooled in an ice bath. Triethylamine (1.21 g, 12 mmol) was added and then ethyl chloroformate (1.52 g, 14 mmol). After 10 mins the ice bath was removed and after a further 10 mins the mixture filtered into a solution of N1,N7-diethylenetriamine-bislactobionamide (7.84 g, 10 mmol) in DMF at 50° C., washing the residue with ether. The reaction mixture was heated at 50° C. for 4 hours. Solvent was removed by evaporation under reduced pressure, the product washed with ether, collected by buchner filtration and dried under high vacuum, to give N4-octadecanoyl-N1,N7-diethylenetriaminebislactobionamide, as a beige crystalline solid in 99% yield. Spectroscopic data was consistent with the product.

N4-octadecanoyl-N1,N7-diethylenetriaminebislactobionamide has the structure according to the formulae given above wherein each a, b, c, d, e and g is 1, f is 2, R is $C_{17}H_{35}$, X is CO and Y is galactose.

EXAMPLE 2

Synthesis of N4,N7-Ditridecanoyl-N1,N10-Triethylenetetraminebislactobionamide (2)

Triethylenetetramine (1.46 g, 10 mmol) and lactobionic acid (7.52 g, 21 mmol) were dissolved in methanol (750 ml) and heated under reflux for 24 hours. The solution was cooled, and the solvent evaporated under reduced pressure and product freeze dried to give N1,N10-triethylenetetramine-bislactobionamide as a crystalline yellow solid in 98% yield. Spectroscopic data was consistent with the product.

Tridecanoic acid (4.72 g, 22 mmol) was dissolved in diethyl ether (10 ml) and cooled in an ice bath. Triethylamine (2.23 g, 22 mmol) was added and then ethyl chloroformate (2.60 g, 24 mmol). After 10 mins the ice bath was removed and after a further 10 mins the mixture was filtered into a solution of N1,N10-triethylenetetramine-bislactobionamide (8.28 g, 10 mmol) in DMF at 50° C., washing the residue with ether. The reaction mixture was heated at 50° C. for 4 hours. Solvent was removed by evaporation under reduced pressure, the product washed with ether, collected by buchner filtration and dried under high vacuum, to give N4,N7-ditridecanoyl-N1,N10 -triethylenetetramine-bislactobionamide, as a yellow crystalline powder in 81% yield. Spectroscopic data was consistent with the product.

N4,N7-ditridecanoyl-N1,N10 -triethylenetetramine-bislactobionamide has the structure according to the formulae given above wherein each a, b, c, d and g is 1, each of e and f is 2, R is $C_{12}H_{25}$, X is CO and Y is galactose.

EXAMPLE 3

Synthesis of N4,N7-Didodecylisocyano-N1,N10-Triethylenetetraminebislactobionamide (3)

Dodecyl isocyanate (4.64 g, 22 mmol) was added to a solution of N1,N10-triethylenetetraminebislactobionamide (8.28 g, 10 mmol) in DMF at 50° C. The reaction mixture was heated at 50° C. for 4 hours. Solvent was removed by evaporation under reduced pressure, the product washed with ether, collected by buchner filtration and dried under high vacuum, to give N4,N7-didodecylisocyano-N1,N10-triethylenetetraminebislactobionamide, as a yellow crystalline powder in 92% yield. Spectroscopic data was consistent with the product.

N4,N7-didodecylisocyano-N1,N10 -triethylenetetraminebislactobionamide has the structure according to the formulae given above wherein each a, b, c, d and g is 1, each of e and f is 2, R is $C_{12}H_{25}$, X is NHCO and Y is galactose.

EXAMPLE 4

Synthesis of N4,N7-Diphenylundecanoyl-N1,N10-triethylenetetraminebislactobionamide (4)

Following the procedure of Example 2, N4,N7 -diphenylundecanoyl-N1,N10-triethylenetetraminebislactobionamide was also made and collected as an orange crystalline powder in 81% yield. Spectroscopic data was consistent with the product.

N4,N7-Diphenylundecanoyl-N1,N10 -triethylenetetramine-bislactobionamide has the structure according to the formulae given above wherein each a, b, c, d and g is 1, each of e and f is 2, R is $(C_6H_5)C_{10}H_{20}$, X is CO and Y is galactose.

EXAMPLE 5

Synthesis of N4,N7-didodecanoyl-N1,N10-triethylenetetraminebi slactobionamide (5)

Triethylenetetramine (1.46 g, 10 mmol, hydrate 98%, dried before use) and lactobionic acid (7.17 g,20 mmol) were dissolved in DMF (dimethylformamide, 50 ml, anhydrous 99.8%, stored under nitrogen) and heated at 50° C. under argon for 24 hours. The solution was cooled, and the solvent evaporated under reduced pressure to give N1,N10-triethylenetetraminebislactobionamide as a crystalline yellow solid in 98% yield. Spectroscopic data was consistent with the product.

Dodecanoic acid (4.01 g, 20 mmol) was dissolved in diethyl ether (10 ml) and cooled in an ice bath. Triethylamine (2.02 g,20 mmol) was added and then ethyl chloroformate (2.17 g,20 mmol). After 10 mins the ice bath was removed and after a further 10 mins the mixture was filtered into a solution of N1,N10-triethylenetetraminebislactobionamide (8.28 g, 10 mmol) in DMF at 50° C., washing the residue with ether. The reaction mixture was heated at 50° C. for 4 hours. Solvent was removed by evaporation under reduced pressure, the product washed with ether, collected by Buchner filtration and dried under high vacuum. The product was dissolved in distilled water (40 ml) and stirred with Amberlite IRA-420(OH) resin at pH=10 for 40 mins. The resin was removed by Buchner filtration and the product was obtained after freeze drying overnight. The product was briefly washed with ethyl acetate and dried on the vacuum line. N4,N7 -didodecanoyl-N1,N10-triethylenetetraminebislactobionamide was collected as a yellow powder in about 40% yield. Spectroscopic data was consistent with the product.

N4,N7-didodecanoyl-N1,N10-triethylenetetraminebislactobionamide has the structure according to the formulae given above wherein each a, b, c, d and g is 1, each of e and f is 2, R is $C_{11}H_{23}$, X is CO and Y is galactose.

EXAMPLE 6

Synthesis of N4,N7-ditetradecanoyl-N1,N10-triethylenetetraminebislactobionamide (6)

Compound 6 was prepared by the method of Example 5 using tetradecanoic acid (4.57 g, 20 mmol) and was collected as a yellow powder in about 40% yield.

EXAMPLE 7

The surface tension lowering property of compounds of the invention was measured at 40° C. in aqueous gelatin (7% by weight deionised gelatin in water). Concentrations of surfactant ranging from 0.01 to 0.30 weight percent were used. The surface tension values ($mN^{-1}$) are shown below.

|  | Wt % surfactant | | | |
| --- | --- | --- | --- | --- |
|  | 0.01 | 0.03 | 0.10 | 0.30 |
| Compound (1) | 50.23 | 45.60 | 45.06 | 44.03 |
| Compound (2) | 50.25 | 39.23 | 36.83 | 36.17 |
| Compound (3) | 52.77 | 45.58 | 41.20 | 40.53 |
| Compound (4) | 37.47 | 36.57 | 35.73 | 35.97 |
| Compound (5) | 35.80 | 35.57 | 34.07 | 33.80 |
| Compound (6) | 52.20 | 45.70 | 37.60 | 47.13 |

EXAMPLE 8

The compounds of the invention show rheology modifying properties and lower the viscosity of disperse systems stabilised by ionic surfactants and polymers.

A comparison was made between compounds of the invention and 1,2-bis-N-methylgluconamidotridecane (a good rheology modifier) as modifiers of the viscosity of 10% by weight deionised gelatin solutions containing 1% weight sodium dodecylsulphate (SDS). Viscosity was measured at low shear rates on a Bohlin CS50 rheometer at 40° C. using the double-concentric-cylinder DG 24/27 geometry. The concentration of surfactant was 0.5% by weight in all cases.

| Sample | Viscosity (mPa · s) |
| --- | --- |
| Control | 286 |
| 1,2-bis-N-methylgluconamidotridecane | 196 |
| Compound 2 | 259 |
| Compound 4 | 228 |
| Compound 5 | 235 |
| Compound 6 | 265 |

We claim:

1. A photographic material comprising a support having thereon at least one layer comprising a hydrophilic colloid and a water-soluble or water-dispersible, non-ionic surface active compound according to the formula $$\overset{R}{\underset{X}{|}} \\ ZNH(CH_2)_a[(CH_2)_bN(CH_2)_c]_e(CH_2)_dNHZ \quad (II)$$

wherein

R is a hydrophobic hydrocarbon group;

X is a linking group;

a, b, c and d each independently represents an integer from 1 to 5;

e represents an integer from 1 to 8; and,

Z is a disaccharide group represented by the structure

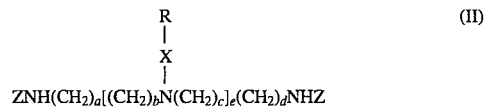

wherein

Y is a monosaccharide; and, f and g each independently represents 0 or an integer from 1 to 3 provided that the sum of f and g is 3.

2. A photographic material according to claim 1 wherein Y is glucose, galactose or mannose.

3. A photographic material according to claim 1 wherein each R group is an alkyl, alkenyl, allyl or aryl group.

4. A photographic material according to claim 1 wherein each R group contains from 10 to 20 carbon atoms.

5. A photographic material according to claim 1 wherein the total number of carbon atoms in the hydrophobic hydrocarbon groups is from 10 to 40.

6. A photographic material according to claim 1 wherein the linking group X is selected from

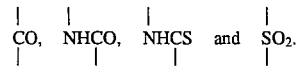

7. A photographic material according to claim 1 wherein e is an integer from 1 to 4.

* * * * *